(12) United States Patent
Le Moal et al.

(10) Patent No.: US 8,861,831 B2
(45) Date of Patent: Oct. 14, 2014

(54) METHOD FOR ANALYZING THE QUALITY OF A GLAZING UNIT

(75) Inventors: Simon Le Moal, Paris (FR); Corinne Payen, Montmacq (FR)

(73) Assignee: Saint-Gobain Glass France, Courbevoie (FR)

( * ) Notice: Subject to any disclaimer, the term of this patent is extended or adjusted under 35 U.S.C. 154(b) by 231 days.

(21) Appl. No.: 13/503,159

(22) PCT Filed: Oct. 15, 2010

(86) PCT No.: PCT/FR2010/052185
§ 371 (c)(1),
(2), (4) Date: Apr. 20, 2012

(87) PCT Pub. No.: WO2011/048306
PCT Pub. Date: Apr. 28, 2011

(65) Prior Publication Data
US 2012/0207380 A1    Aug. 16, 2012

(30) Foreign Application Priority Data

Oct. 21, 2009 (FR) ..................................... 09 57398
May 6, 2010 (FR) ..................................... 10 53558

(51) Int. Cl.
*G01N 21/86* (2006.01)
*G01N 21/00* (2006.01)
*G01B 11/25* (2006.01)
*G01N 21/958* (2006.01)

(52) U.S. Cl.
CPC ........ *G01B 11/25* (2013.01); *G01N 2021/9586* (2013.01); *G01N 21/958* (2013.01)
USPC ..................... 382/141; 250/559.01; 356/239.7

(58) Field of Classification Search
USPC ................ 382/141; 250/221, 559.01, 559.04, 250/559.05, 559.07, 559.19, 559.22; 356/239.1, 239.7, 600–602, 605, 610, 356/630
See application file for complete search history.

(56) References Cited

U.S. PATENT DOCUMENTS

| 4,853,777 | A | * | 8/1989 | Hupp | 348/128 |
| 5,067,817 | A | * | 11/1991 | Glenn | 356/613 |
| 5,085,516 | A | * | 2/1992 | Bertrand et al. | 356/394 |
| 5,568,258 | A | * | 10/1996 | Uemura et al. | 356/237.1 |
| 5,835,223 | A | * | 11/1998 | Zwemer et al. | 356/600 |

(Continued)

FOREIGN PATENT DOCUMENTS

DE    196 43 018    4/1998

OTHER PUBLICATIONS

International Search Report Issued Feb. 22, 2011 in PCT/FR10/52185 Filed Oct. 15, 2010.

*Primary Examiner* — Sheela Chawan
(74) *Attorney, Agent, or Firm* — Oblon, Spivak, McClelland, Maier & Neustadt, L.L.P.

(57) ABSTRACT

A method for analyzing quality of a glazing unit including: generating a digital image of a test chart produced in reflection by an outer surface of the glazing, the test chart presenting a pattern composed of a plurality of contrasted elements defining between them interface lines; calculating quantities representative of the glazing from the image generated, the calculation being carried out by a processing unit; and comparing the calculated values for the representative values relative to reference values. The representative quantities are representative of a deformation of the image of the test chart produced in reflection by the outer surface of the glazing.

27 Claims, 8 Drawing Sheets

(56) References Cited

U.S. PATENT DOCUMENTS

| | | |
|---|---|---|
| 6,100,990 A | 8/2000 | Ladewski |
| 6,122,065 A * | 9/2000 | Gauthier .................. 356/394 |
| 6,376,829 B1 * | 4/2002 | Okugawa .................. 250/225 |
| 6,392,754 B1 * | 5/2002 | Pingel et al. .................. 356/603 |
| 6,433,353 B2 * | 8/2002 | Okugawa .................. 250/559.4 |
| 7,430,049 B2 * | 9/2008 | Bertin-Mourot et al. ...... 356/605 |
| 7,471,383 B2 * | 12/2008 | Ehrick .................. 356/239.1 |
| 7,589,844 B2 * | 9/2009 | Hirata et al. .................. 356/601 |
| 2006/0050284 A1 | 3/2006 | Bertin-Mourot et al. |
| 2008/0316501 A1 * | 12/2008 | Hirata et al. .................. 356/601 |

* cited by examiner

METHOD FOR ANALYZING THE QUALITY OF A GLAZING UNIT

TECHNICAL FIELD

The present invention relates to the field of analysis of the quality of glazing units, notably automobile glazing units.

The present invention relates more particularly to a method for analyzing the quality of glazing, comprising:
- a step of generating a digital image of a test chart produced in reflection by the glazing, the test chart presenting a pattern composed of a plurality of contrasted elements defining between them interface lines;
- a step of calculating the quantities representative of the glazing from the image generated, the calculation being carried out by a processing unit; and
- a step of comparing the calculated values for the representative quantities relative to reference values.

BACKGROUND

WO-A-02/42715 describes a method for analyzing the surface of a glazing unit consisting of extracting, by digital processing for each pixel of the digitized image, local phases in two directions. Variations of local phases make it possible to calculate variations of local slopes of the surface of the glazing so as to deduce therefrom variations in the curvature or variations in the height of the surface.

It is possible, by comparing variations in the curvature of the glazing with reference quantities, to proceed to a choice as to whether to reject the glazing.

Nevertheless, although this possible selection criterion certainly makes it possible to judge the curvature of the glazing it does not necessarily make it possible to judge the esthetic quality of the image produced in reflection by the glazing. In point of fact, according to the position of the observer, a surface defect will not have the same effect on the image in reflection.

If an attempt is made to use such a method for judging the esthetic quality of the glazing in reflection, some glazing units would sometimes be rejected without, for all that, being really prejudicial esthetically or vice versa.

Moreover, with a method of this type, the calculated quantities on the edges of the glazing are not generally reliable.

Finally, this type of method requires long and difficult calibration.

WO-A-2007/115621 and U.S. Pat. No. 6,392,754 also describe methods aimed at measuring the shape of the surface of the glazing. These methods notably have the same disadvantage as regards the relevance of the assessment of the esthetic quality of the glazing.

SUMMARY

One object of the invention is to provide a method for analyzing the quality of the image produced in reflection by a glazing unit that makes it possible to choose whether to reject the glazing on the basis of technical criteria that are relevant for the assessment of the esthetic quality in reflection of the glazing.

To this end, the subject of the invention is a method for analyzing the quality of a glazing unit, comprising:
- a step of generating a digital image of a test chart produced in reflection by the outer surface of the glazing in the direction away from the glazing, the test chart presenting a pattern composed of a plurality of contrasted elements defining between them interface lines;
- a step of calculating the quantities representative of the glazing from the image generated, the calculation being carried out by a processing unit; and
- a step of comparing the calculated values for the representative quantities relative to reference values; characterized in that the representative quantities are representative of the deformation of the image of the test chart produced in reflection by the outer surface of the glazing.

The invention has the advantage of making it possible to judge the quality of the image in reflection produced by a glazing unit, not from dimensional characteristics of the glazing, but on the basis of the image in reflection produced by the outer surface of the glazing from the outside. The choice of whether to reject the glazing is then relevant from the point of view of the assessment of the esthetic quality of the image produced in reflection outward by the glazing.

By virtue of the invention, the glazing is prevented from being rejected when it presents a geometric defect that is not visible and/or that is not judged to be unesthetic. Conversely, a glazing unit that does not present a serious surface defect but all the same produces an appreciable esthetic defect in the image produced in reflection will be better selected.

The invention moreover makes it possible to evaluate defects over the entire zone of the glazing, notably on the edges of the glazing.

The invention also makes analysis possible without calibration.

According to particular embodiments, the method according to the invention comprises one or more of the following characteristics, taken in isolation or in all technically possible combinations:
- the representative quantities are representative of a deformation of interface lines of the image of the test chart produced in reflection by the outer surface of the glazing;
- the representative quantities are representative of a deformation of each interface line of the image of the test chart produced in reflection by the outer surface of the glazing, in a zone of the glazing;
- the contrasted elements are alternate dark and light bands defining between them parallel interface lines, the interface lines being oriented so as to form an angle of between 20° and 70° with an anticipated direction of a defect of the glazing in a predetermined zone of the glazing, preferably an angle between 20° and 60°, preferably between 40° and 60°, preferably approximately 45°;
- at least one of said representative quantities is a statistical quantity;
- the statistical quantity is chosen from the following quantities, taken in isolation or in any possible combination: a mean, a weighted mean, a median, a standard deviation, a number of occurrences above or below a reference value, a maximum or a minimum;
- said representative quantities comprise a quantity representative of a value for the orientation of at least one line representative of a principal orientation of at least one contrasted element and/or a quantity representative of a local variation of the orientation of at least one line representative of a principal orientation of at least one contrasted element and/or a quantity representative of a dimension of at least one contrasted element and/or a representative quantity of a local variation relative to a dimension of at least one contrasted element;
- the local variation of the line representative of the principal orientation of the contrasted element comprises the calculation of o(Pk+s)−o(Pk), s being the chosen step, o(Pk) being the value for the orientation of the line representative of a principal orientation of the contrasted element at pixel Pk of the index k;

the line representative of a principal orientation of the contrasted element is one of the interface lines at least partially delimiting the contrasted element;

the line representative of a principal orientation of a band (12) is one of the interface lines (13) delimiting the band (12);

said dimension is a local thickness e(Pk) of the contrasted element or a distance between two contrasted elements;

the local thickness is calculated by the distance between two adjacent interface lines;

the degree of relative local variation of said dimension comprises calculating e(Pk+s)−e(Pk) with e(Pk) the value of said dimension of the contrasted element at pixel Pk of index k, s being the step of the degree of variation;

the calculation is repeated for several interface lines and/or several contrasted elements;

the calculation is repeated inside one or more predefined zones for analyzing the image;

the method is repeated with at least one supplementary image, different from the first image;

the supplementary image is obtained for a test chart of which the contrasted elements are alternate dark and light bands defining between them parallel interface lines (13), but forming an angle of between 30° and 150° with the direction of the interface lines (13) of the test chart used in order to obtain the first image, preferably an angle of between 60° and 120°, even more preferably between 80° and 100°, preferably approximately 90°;

the interface lines (13) of the test chart used for the second image are oriented so as to form an angle of between 20° and 70° with an anticipated direction of a defect of the glazing in a predetermined zone of the glazing, preferably an angle between 20° and 60°, preferably between 40° and 60°, preferably approximately 45°;

the angle of incidence between the apparatus and the normal to the plane of the glazing lies between 0° and 90°, preferably between 40° and 70° for a lateral glazing unit of a motor vehicle and preferably between 60° and 80° for a motor vehicle roof;

the angle of incidence between the axis of the apparatus and the normal to the plane of the glazing is equal to the angle between the plane of the test chart and the plane of the glazing;

the contrasted elements are bands and/or squares and/or spots;

the step of generating the image comprises:
  a step of exposing the glazing to a test chart having a pattern composed of a plurality of contrasted elements defining between them interface lines;
  a step of digital acquisition, by an apparatus with digital sensors, of the image reflected by the glazing toward the apparatus.

the image of a test chart produced in reflection by the glazing is obtained by a simulation from the outer surface of the glazing, for example from a theoretical surface of the glazing, from a measured surface of the glazing or from a surface obtained by simulation of the curvature of the glazing; and the method includes a step of choosing whether to reject the glazing according to the result of the comparison.

Another subject of the invention is a method for producing a glazing unit comprising a method for forming the glazing followed by a method for analyzing the quality of the glazing formed, characterized in that the method for analyzing quality is as described above.

According to particular embodiments, the method for producing the glazing according to the invention comprises one or more of the following characteristics, taken in isolation or according to all technically possible combinations:

the method for forming the glazing comprises a step of shaping the glazing defining said anticipated direction of a defect of the glazing in a predetermined zone;

the step of shaping the glazing comprises a step of contacting with at least one roller, the anticipated direction of the defect being along the axis of the roller or perpendicular to this direction;

the step of shaping the glazing comprises the step of holding the edges of the glazing, for example for pressing or for allowing the glazing to sink under gravity, the anticipated direction of the defects in the region of the edges being parallel to or perpendicular to the respective edge.

The subject of the invention is also a device for analyzing the quality of a glazing unit, comprising means for generating a digital image of a test chart produced in reflection by the outer surface of the glazing in a direction away from the glazing and a processing unit for processing the image generated, the processing unit comprising a memory and a computer, characterized in that the device is able to implement the quality analysis method as described above, the memory comprising programs capable of implementing the quality analysis method described above, the programs being able to calculate the representative quantities of the glazing from the image generated, the representative quantities being representative of the deformation of the image of the test chart produced in reflection by the outer surface of the glazing.

According to a particular embodiment of the device, the means for generating the image comprise a test chart and an apparatus with digital sensors, the test chart and the apparatus being arranged so as to respectively produce and acquire the image of the test chart produced in reflection by the outer surface of the glazing, the test chart being for example a screen, the device comprising for example a projector for projecting test chart patterns onto the screen.

BRIEF DESCRIPTION OF THE DRAWINGS

The invention will be better understood on reading the following description, given solely by way of example, made with reference to the appended drawings, in which.

DETAILED DESCRIPTION

Figure 1:
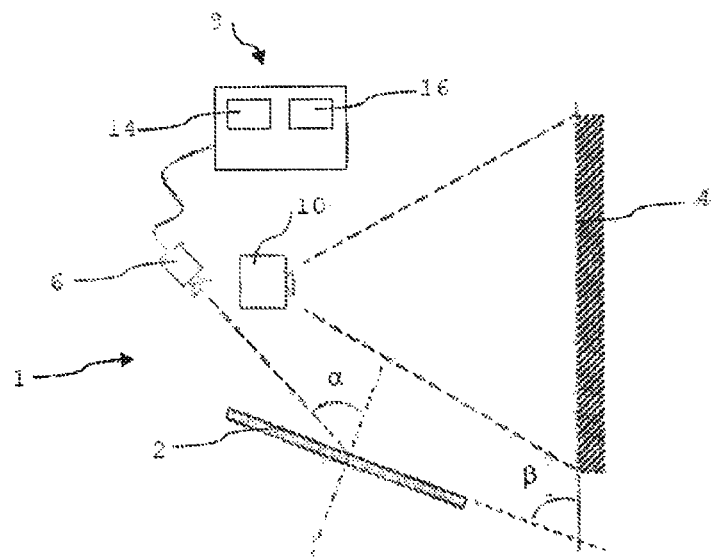
FIG. 1 is a schematic view illustrating the device for analyzing the quality of a glazing unit, according to the invention.

FIG. 1 illustrates a device 1 according to the invention suitable for carrying out an analysis of the image produced in reflection by the outer surface of a glazing unit 2.

The device comprises a test chart 4, a digital camera 6 and a unit 8 for processing the image produced by the apparatus 6.

Figure 2:
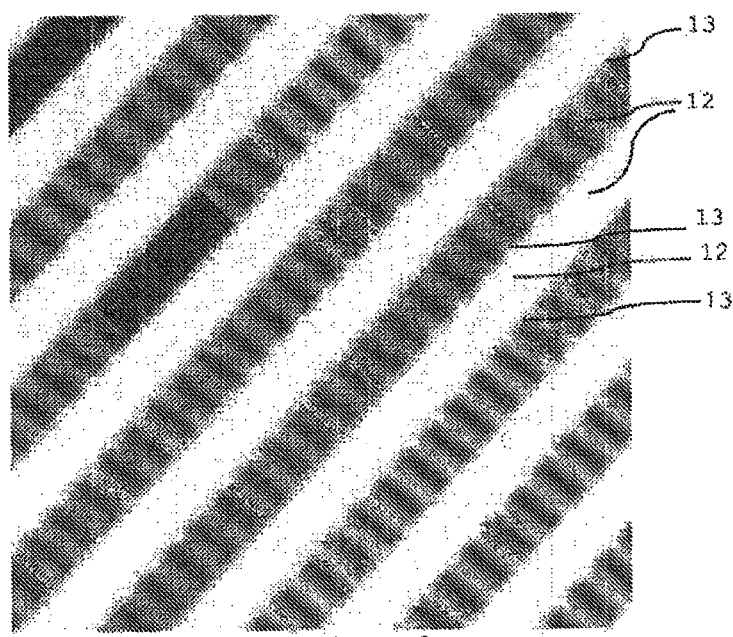
FIG. 2 is an enlarged view illustrating an example of the test chart pattern.

The test chart 4 is here a screen on which an image is projected by a projector 10. This image is for example, as illustrated in FIG. 2, a pattern of alternate light and dark bands. It consists more generally of a pattern composed of a plurality of contrasted elements 12 defining between them an interface line 13.

The test chart 4 is preferably flat. It extends for example in a plane forming an angle of between 0° and 90° with the surface of the glazing 2. This angle lies for example between 40° and 70° for a side glazing unit of a motor vehicle, for example approximately 60°, so as to be as close as possible to real observation conditions. For a motor vehicle roof, this angle will lie for example between 60° and 80°, for example approximately 75°. A larger angle, at 40° for example, makes it possible to reduce any disturbances due to secondary reflections.

The digital apparatus 6, which is for example a camera (or photographic apparatus) with CCD sensors, is arranged so as to receive the image of the test chart 4 in reflection. In the example illustrated, the apparatus 6 is placed in the direction opposite to the test chart 4 relative to the glazing 2.

The angle $\alpha$ between the axis of the digital apparatus 6 and the normal to the plane of the glazing 2 is equal to the angle $\beta$ between the plane of the test chart 4 and the plane of the glazing 2.

In the case of an inwardly curved glazing unit, the plane of the glazing 4 will be considered for example as the plane tangential to the center of the glazing 2.

The digital apparatus 6 provides the processing unit 8 with a digitized image of the image in reflection of the test chart 4 produced by the glazing 2.

Figure 3:
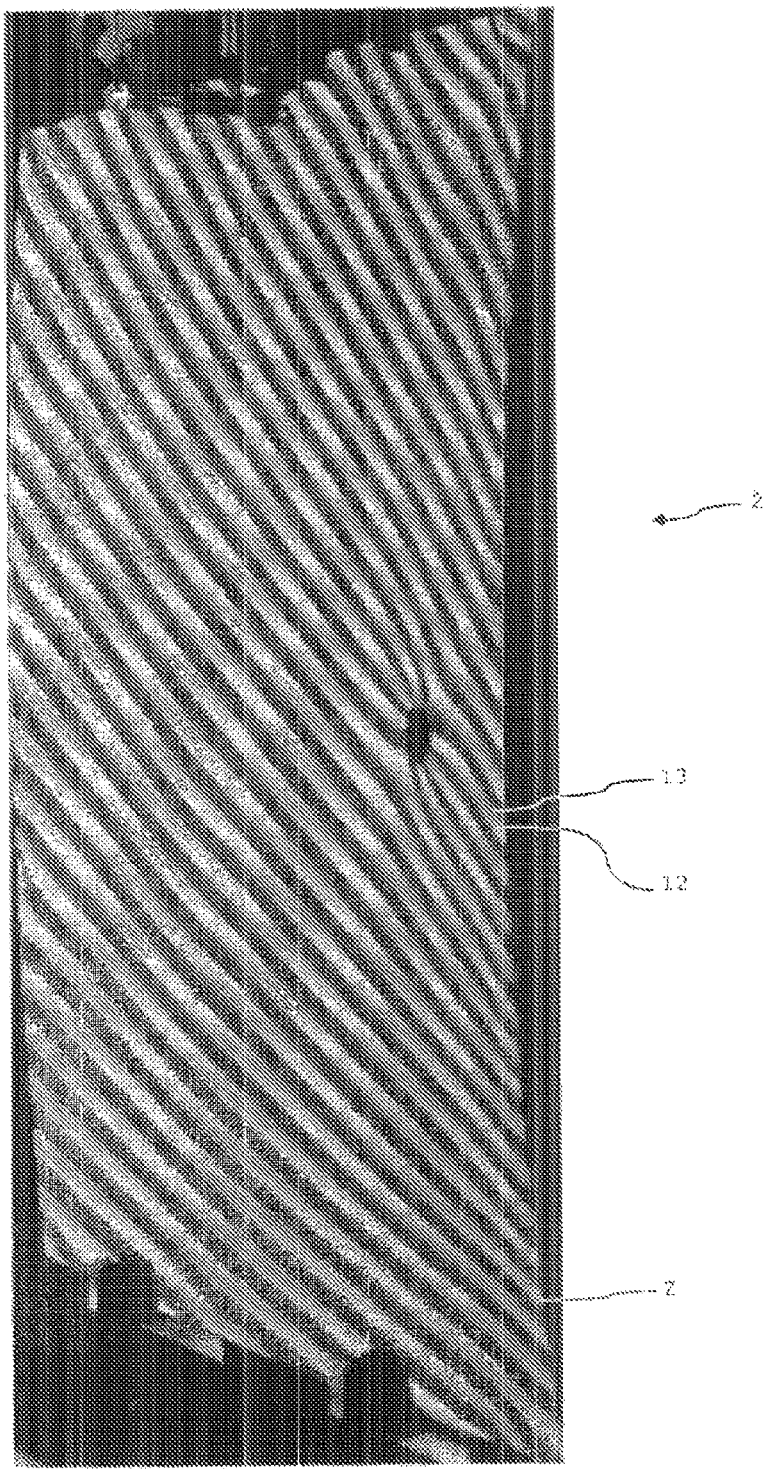
FIGS. 3 and 4 are views illustrating the raw digital images obtained in reflection by two different glazing units with the device of FIG. 1 and the pattern of FIG. 2, the glazing of FIG. 3 exhibiting no major defects while the glazing of FIG. 4 exhibits these.
Figure 4:
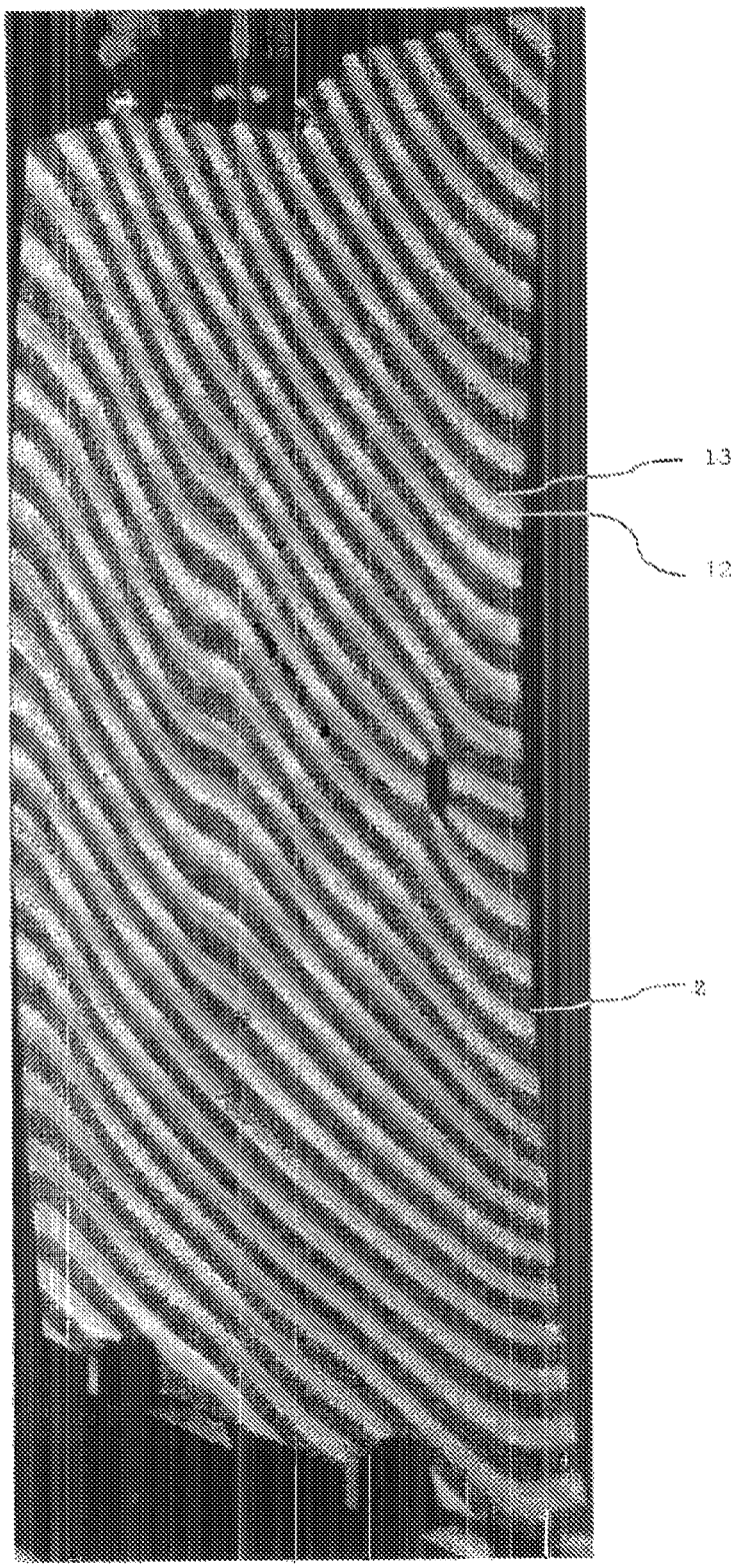

The raw images produced by each glazing 2 are illustrated respectively in FIGS. 3 and 4 for two analog glazing units 2 that exhibit different quality levels in reflection. In this example, motor vehicle roofs are particularly concerned.

The digitally acquired image is then processed in an automated manner by the processing unit 8, for at least one predefined zone Z of the image. It should be noted that, in the example shown in FIGS. 3 and 4, the zone Z corresponds to the entire image produced by the glazing, but it may consist of several distinct zones Z, notably disconnected.

The processing unit 8 comprises a memory 14 on which the processing programs are recorded, and a computer 16 capable of performing processing programs.

The processing programs are able to perform, by means of the computer 16, calculations for quantities representative of a deformation of the image produced in reflection by the glazing 2.

The representative quantities are then used in order to choose whether to reject the glazing 2 according to the result of the comparison between the quantities calculated for the corresponding glazing 2 and the reference quantities.

The reference quantities are obtained for example by measuring and calculating on reference samples.

The representative quantities are more particularly, in the example described, a statistical quantity of a local variation in the orientation of the interface lines and/or a statistical quantity of a relative local variation of the thickness of contrasted elements. More generally, according to the invention, it is a question of quantities representative of a local variation in orientation of a line representative of a principal orientation of at least one contrasted element and/or of quantities representative of a relative local variation of a linear dimension of at least one contrasted element. The line representative of a principal orientation of a contrasted element is here one of the interface lines delimiting the contrasted element.

It is thus a question, more generally and according to the invention, of quantities representative of a deformation of the image produced in reflection by the glazing 2, notably representative of deformations of contrasted elements and/or of interface lines. Statistical quantities other than those mentioned above may be envisaged as explained in the variants described below.

The local variation of the orientation of an interface line is calculated by a degree of local variation of the interface line or by a quantity proportional to this degree.

The program is thus able to calculate, for each pixel Pk of index k of the interface line (13), the quantity $To(Pk)=[o(Pk+s)-o(Pk)]/s$, s being the chosen step and $o(Pk)$ being the quantity of the local orientation of the interface line at pixel Pk.

For the calculation, $o(Pk)$ has been chosen as being the quantity for the orientation of the normal to the interface line at pixel Pk. As a variant, it may of course consist of the quantity of the orientation of the tangent or of any refined function of the quantity of the orientation of the normal.

The calculation of $To(Pk)$ is then repeated for each pixel Pk of the interface line 13 and then repeated for each band 12, inside the predetermined analysis zone Z.

Figure 5:
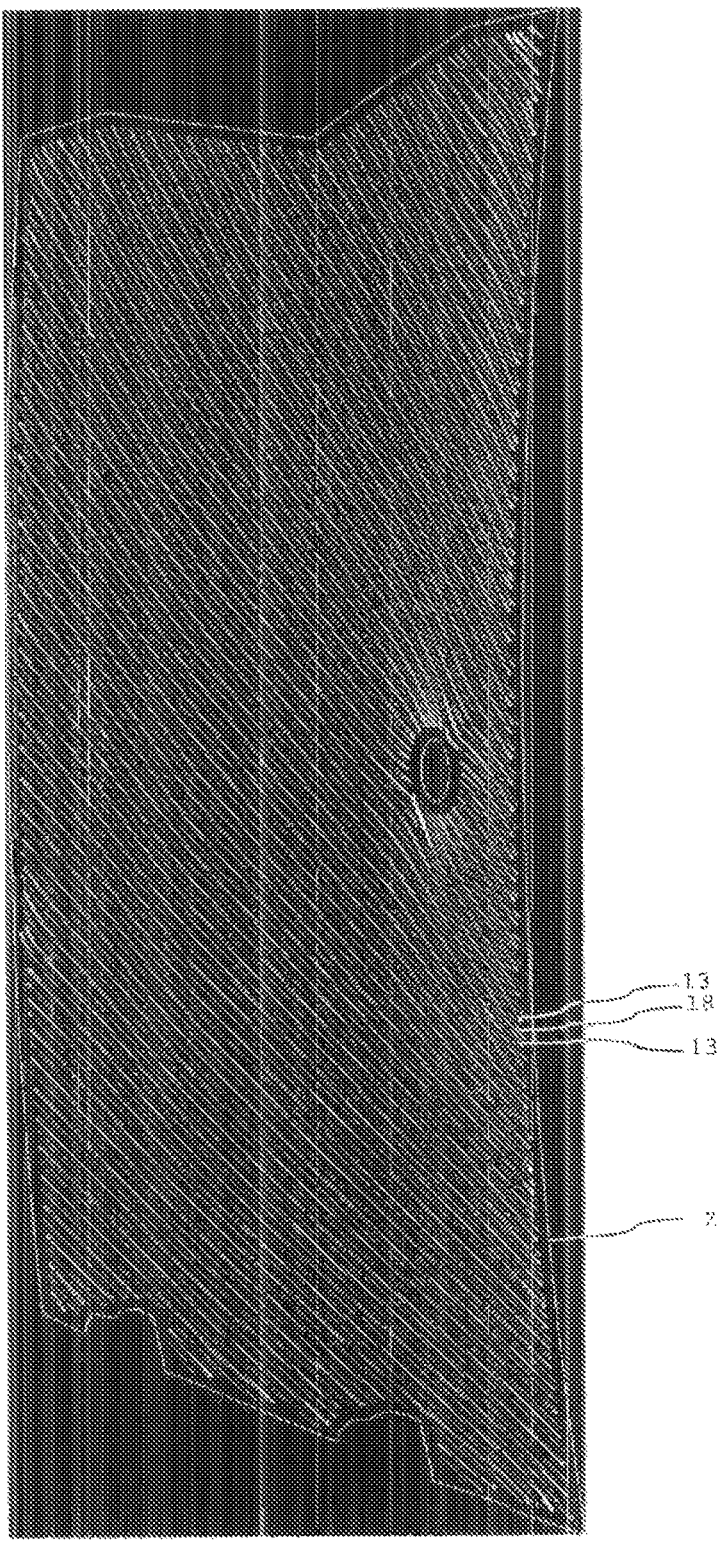
FIGS. 5 and 6 illustrate respectively the images of FIGS. 3 and 4 after processing by an algorithm according to the invention.
Figure 6:
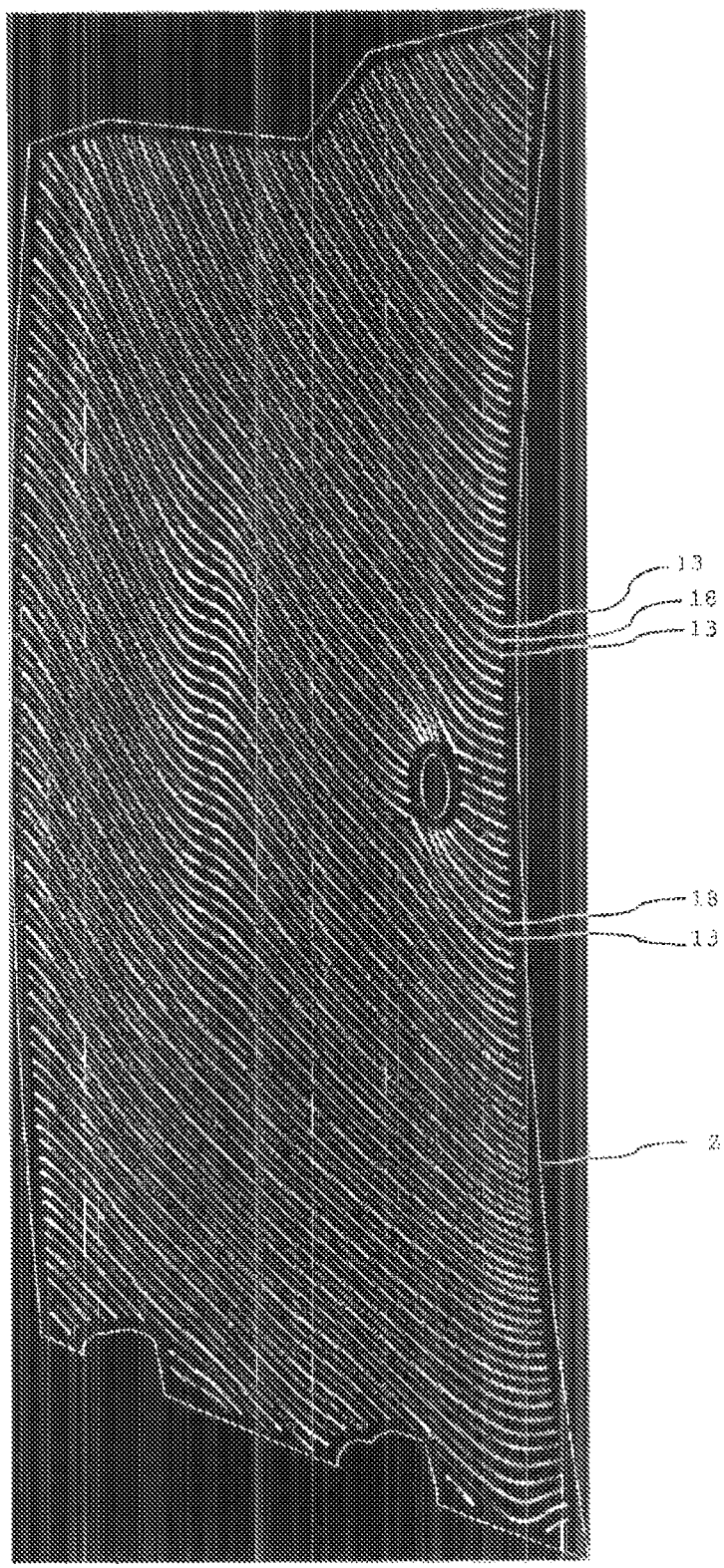

FIGS. 5 and 6 illustrate the images respectively of FIGS. 3 and 4 after processing. The interface lines are more particularly visible, delimiting between them the bands 12 as well as the median line 18 of the bands 12.

In order to bring out visually the quantities of the degree of variation, each pixel of the interface lines 13 shown in FIGS. 5 and 6 has been colored according to its quantity. The pixels corresponding to high quantities of the degree thus appear lighter.

In a step following the calculation, the program has the capability of enabling the processing unit 8 to calculate a mean Mo of the degree of variation To of each pixel of the interface lines 13, inside each analysis zone Z.

The quantity of Mo is compared with a reference quantity for each glazing unit 2 and each analysis zone Z. The processing programs of the unit 8 are for example capable of carrying out this comparison. The reference quantities are defined for each zone Z and are for example different for different zones Z.

The quantity of Mo obtained for the glazing 2 of FIG. 4 is greater than the quantity of Mo for the glazing 2 of FIG. 3. The glazing 2 of FIG. 3 will thus for example be considered as having a better esthetic quality in reflection.

The result of the comparison will lead for example to the rejection of the glazing 2 of FIG. 4 while the glazing 2 of FIG. 3 will be retained. The glazing 2 of FIG. 3 will then pass other tests for example.

Figure 7:
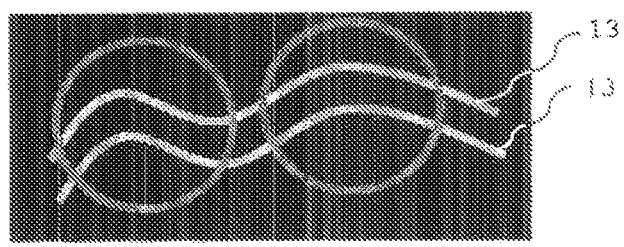
FIGS. 7 and 8 are schematic views illustrating two types of deformation analyzed.

As an example, FIG. 7 illustrates a type of deformation revealed by calculating the degree of local variation in orientation.

The second statistical quantity used in the present example is the relative local variation in the linear dimension of the contrasted element 12. The linear dimension has been chosen here as being the local thickness of the bands 12.

As explained above, each band 12 is delimited by a first interface line 13 and a second interface line 13. Each band 12 possesses a median line 18 as referred to above.

The median line 18 of a band 12 is the line of which each pixel Pk is equidistant from the interface lines 13 delimiting the band 12.

The local thickness e(Pk) is calculated in this example for each pixel Pk of the median line 18 of each band 12 of the analysis zone Z. It consists of double the distance between the pixel Pk of the median line 18 and one of the interface lines 13 of the band 12.

The calculation of e(Pk) is repeated for each pixel Pk of index k of the median line 18 and then repeated for each band 12, inside each analysis zone Z.

The quantity of e(Pk) is stored in the memory 14 and associated with the corresponding pixel Pk.

The degree of relative local variation of the linear dimension is then calculated by Te(Pk)=[e(Pk+s)−e(Pk)]/[s·e(Pk)] for the pixel Pk of index k of the median line 18, with s being the step of the degree of variation.

The calculation of Te(Pk) is then repeated, inside each zone Z, for each pixel Pk of index k of the median line 18 of each band 12 and for each band 12 of the zone Z.

Then, the program is capable of ensuring that the processing unit 8 calculates the mean Me of the degree of variation Te for all the pixels of the median line 18, inside each analysis zone Z.

In the same way as for the degree of local variation of orientation To, the mean Me is compared with reference values for each zone Z and the choice of whether to reject the glazing is based on the result of this comparison or these comparisons.

Figure 8:
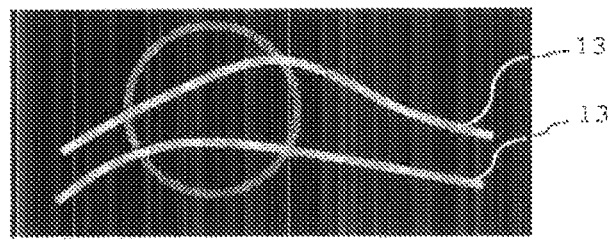

FIG. 8 illustrates an example of a deformation that is revealed by calculating the degree of relative local variation of thickness.

Apart from the device described above, the subject of the invention is also a method implementing the above device, namely, in a general manner, a method comprising:

a step of generating a digital image of a test chart produced in reflection by the outer surface of the glazing in the direction away from the glazing, the test chart presenting a pattern composed of a plurality of contrasted elements defining between them the interface lines;

a step of calculating the quantities representative of the glazing from the image generated, the calculation being carried out by a processing unit; and a step of comparing the quantities calculated for the representative quantities relative to the reference quantities, the representative quantities being representative of a deformation of the image of the test chart produced in reflection by the outer surface of the glazing.

According to particular embodiments, the method according to the invention has the characteristics described above.

As a variant, the method is repeated with at least one supplementary image, for example three supplementary images, in order to make the rejection choice according to the results for the various images. The patterns of the test chart are for example obtained for each of the supplementary images. According to another example, it is the glazing 2 rather than the test chart 4 that is turned in order to generate supplementary images.

Also as a variant, the at least one supplementary image is generated from a test chart offset in translation, relative to the first image, in a direction perpendicular to the preferred direction of the test chart.

Also as a variant, the orientation of the contrasted elements is for example represented by a line parallel to one of the interface lines delimiting the band or parallel to the median line. It may also consist of a line corresponding to a weighted mean of two adjacent interface lines, with for respective coefficients k and 1−k, k being between 0 and 1.

As a further variant, the statistical quantity is a weighted mean, a median, a standard deviation, a maximum, a minimum, a number of occurrences above or below a reference value, and another statistical quantity of any suitable type, or a combination of several of these quantities of any suitable type.

It should be noted however that, even if the statistical quantities are preferred, it may be the case of a variant of raw quantities that are compared directly with the reference quantities.

As a variant, the different number of said analysis zones Z is defined. The number, the position and the extent of the analysis zone or zones Z is chosen from any suitable type.

Also as a variant, the representative quantity is a dimension of the contrasted elements or a statistical quantity of this dimension, and not necessarily a degree of the relative local variation of this dimension. It will thus be possible for example to compare the local quantities of the thickness of the bands with reference values. As a variant, the local quantities of the orientation of the line representative of the orientation will be compared, that is to say the interface line, with reference quantities. The dimension is for example linear (thickness, distance) or areal.

As a further variant, the contrasted elements are bands and/or squares and/or spots and/or one of the geometric elements of any suitable type.

In the case of squares, the dimension is for example a distance between the squares or a size dimension of the squares.

In the case of spots, interest will be more particularly directed to the dimensions of the spots and/or the distance between the spots and/or the orientation of the spots if they are deformed in a preferred direction.

Also as a variant, the image is obtained by simulation from the outer surface of the glazing, for example, from a theoretical surface of the glazing from a measured surface or from a surface obtained by simulation of the curvature of the glazing. The use of a test chart and a digital apparatus is not then necessary.

As a further variant, the image of contrasted elements is not obtained by projection on a screen but by a test chart contrasted in itself.

Also as a variant, the method according to the invention is combined with a method of a known type calculating the height of the outer surface of the glazing. The two methods may in point of fact provide data that is complementary.

Figure 9:
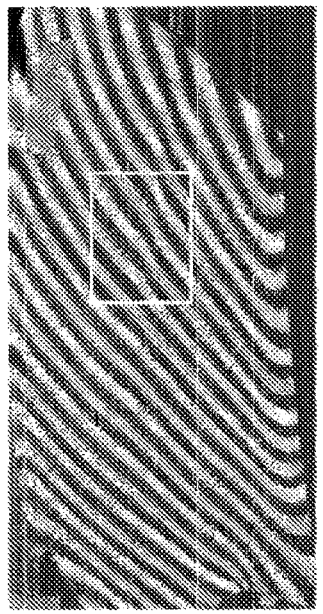
FIGS. 9 and 10 illustrate the image in reflection obtained by the same glazing, according to a variant of the embodiment of the invention in which the test chart pattern is oriented in an advantageous manner.
Figure 10:
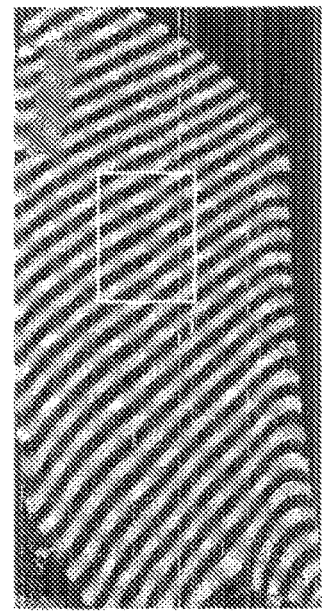

According to an alternative embodiment illustrated in FIGS. 9 and 10, the pattern of the test chart consists of alternate light and dark bands defining between them parallel interface lines that form an angle of 45° with respect to the anticipated direction of defects.

In point of fact, the method very often aims at detecting defects linked to the shaping of the glazing, for example defects generated by contact with rollers (for example a conveyer roller or a forming roller) or only by stretching the glazing when the latter is deformed by gravity (notably on the edges of the glazing). These defects are elongated and always appear in one or more known predetermined zones (for example on the edges) and in a known anticipated direction for each zone (for example the direction of the axis of the rollers or the direction of the edge).

On motor vehicle roofs or windscreens, more generally on glazing units with a substantially rectangular contour, the direction of these defects is substantially parallel to or perpendicular to the edges of these glazing units.

According to this variant, the interface lines of the test chart form an angle of 45° with the anticipated direction of the defect. According to this variant, two images are acquired, one for a first orientation at 45° with respect to the anticipated direction of the defects, and a second, still at 45°, forming an angle of 90° with the pattern of the test chart used for obtaining the first image.

Figure 11:
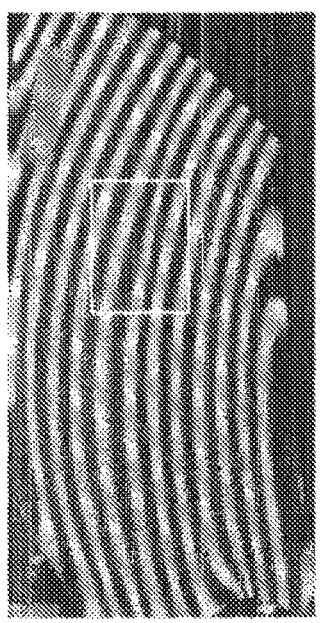
FIGS. 11 and 12 are provided as a comparison relative to FIGS. 9 and 10 and illustrate images obtained for the same glazing but for other orientations of the test chart pattern.
Figure 12:
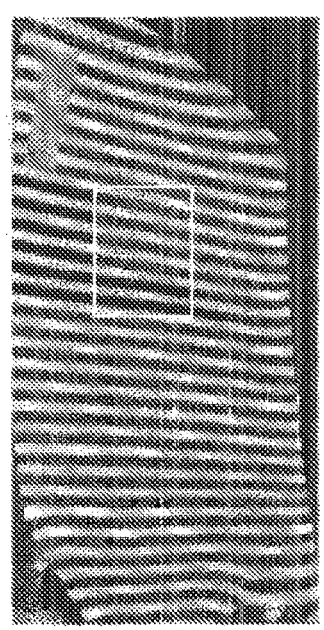

As a comparison, FIGS. 11 and 12 illustrate the patterns of the test chart oriented at 0° or at 90° with respect to the direction of the defects.

The orientation of the test chart according to this variant of the invention (FIGS. 9 and/or 10) have the advantage of guaranteeing that the defect is detected, even if a single image is taken, contrary to the result obtained on FIG. 12 on which the defect is not visible.

Moreover, such an orientation of the bands of the test chart makes it possible to visualize the extent of the defect.

In point of fact, as is visible in FIGS. 9 and 10, it is possible to estimate the width and length of the defect, contrary to FIG. 11, on which the defect is visible but its extent is difficult to assess and FIG. 12, on which the defect is not visible.

Then, such an orientation of the bands is particularly effective when the calculation carried out is that of the local variation in orientation for each interface line considered, or that of the local variation of the thickness of each band considered.

It has then been proved that the calculation becomes particularly reliable as concerns the seriousness of the defect.

The orientation of the bands of the test chart is of course not necessarily exactly 45°. Generally, it is for example between 20° and 70°, preferably between 20° and 60°, preferably between 40° and 60°, preferably approximately 45°.

Figure 13:
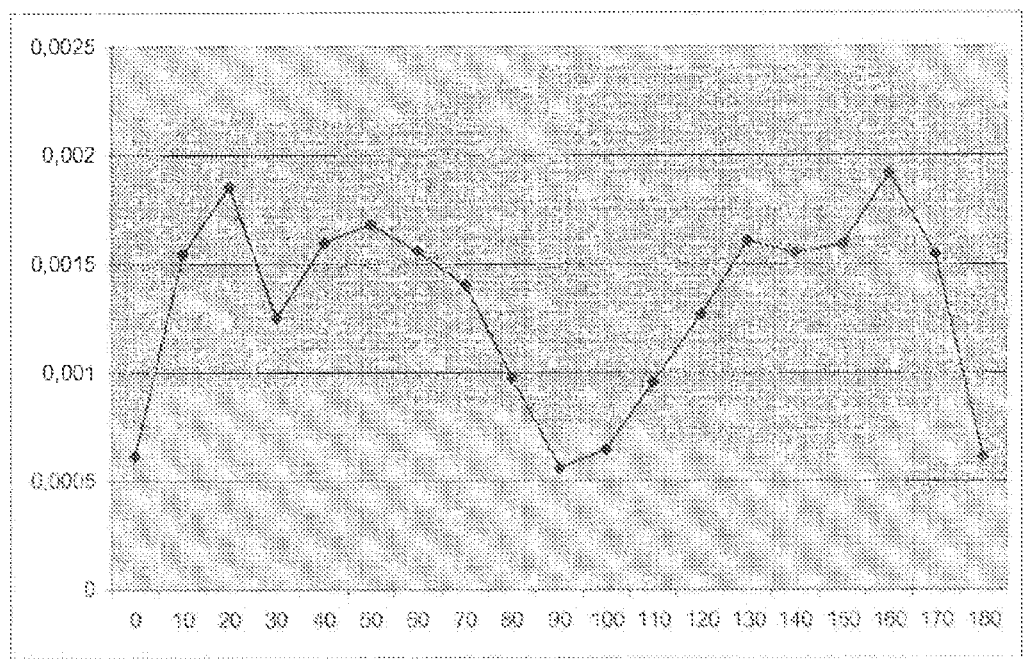
FIG. 13 illustrates the results obtained for calculating the mean of the local variation of orientation, in radians/pixel, as a function of the orientation of the bands of the test chart relative to the defect, in the framed zone of FIGS. 9 to 12.

FIG. 13 illustrates the results obtained for the mean of the local variation of orientation, in radians/pixel, as a function of the orientation of the bands of the test chart with respect to the direction of the defect, in the predetermined zone framed in FIGS. 9 to 12.

To this end, a quantity for the local variation in orientation has been calculated for each pixel of each of the interface lines inside the framed zone. The mean of these quantities has then been calculated. The process was repeated for various orientations of the bands of the test chart with respect to the direction of the defect.

The results shown in FIG. 13 are indicated in the table below:

TABLE 1

| Orientation in degrees of the bands of the test chart with respect to the direction of the defect | Mean of the local variation of the orientation for each pixel of the interface lines inside the framed zone, in radians/pixel |
| --- | --- |
| 0 | 0.00061639 |
| 10 | 0.00154289 |
| 20 | 0.0018542 |
| 30 | 0.00124808 |
| 40 | 0.00159506 |
| 50 | 0.0016801 |
| 60 | 0.00155938 |
| 70 | 0.00139837 |
| 80 | 0.00098004 |

TABLE 1-continued

| Orientation in degrees of the bands of the test chart with respect to the direction of the defect | Mean of the local variation of the orientation for each pixel of the interface lines inside the framed zone, in radians/pixel |
| --- | --- |
| 90 | 0.0005612 |
| 100 | 0.00064534 |
| 110 | 0.00095308 |
| 120 | 0.0012686 |
| 130 | 0.00160588 |
| 140 | 0.00155077 |
| 150 | 0.0015935 |
| 160 | 0.00191364 |
| 170 | 0.00154529 |

As the results of FIG. 13 illustrate, detection of the defect is at an optimum for an orientation between 20° and 70°, then between 110° and 160°, more particularly between 20° and 60° and between 120° and 160°.

The results are symmetrical and it is thus possible to consider that, generally, the angle should lie between 20° and 70°, preferably between 20° and 60°, which is of course equivalent respectively to an angle between 110° and 160°, and between 120° and 160°.

The preferred range between 40° and 60°, preferably approximately 45°, presents the advantage of being more robust with various types of image processing.

It should moreover be noted that although performing the analysis with a single image is possible, performing the analysis with several different images forming between them an angle between 30° and 150°, preferably between 60° and 120°, more preferably between 80° and 100°, preferably approximately 90°, makes detection and quantification of the defect even more reliable. It is a question of a compromise between processing time and the reliability of the diagnosis.

Preferably, each of the two images has an orientation of the bands of the test chart between 20° and 70°, preferably between 20° and 60°, preferably between 40° and 60°, preferably approximately 45° with respect to anticipated direction of the defect.

The analytical method has moreover the advantage that it may be incorporated in a production method with an analysis of the quality of each glazing unit from a production line. Its processing time is in point of fact sufficiently short, for example of the order of 3 seconds for one image, and the analytical device takes up a sufficiently small area.

Finally, it should be noted that the invention may be applied to any motor vehicle glazing unit, notably a side glazing unit, a roof, a windscreen, a rear window, etc.

The invention claimed is:

1. A method for analyzing quality of a glazing comprising:
displaying a test chart;
capturing a digital first image of the test chart produced in reflection by an outer surface of the glazing in a direction away from the glazing, the test chart presenting a pattern including a plurality of contrasted elements defining between them interface lines;
calculating, via a processing unit, values for quantities representative of the glazing from the first image; and
comparing the calculated values for the quantities relative to reference values,
wherein the quantities are representative of deformation of the first image of the test chart produced in reflection by the outer surface of the glazing, and
wherein the values for quantities include one or more of:

a quantity representative of a value for orientation of at least one line representative of a principal orientation of at least one contrasted element, a quantity representative of a local variation of the orientation of at least one line representative of a principal orientation of at least one contrasted element, a quantity representative of a dimension of at least one contrasted element, and a representative quantity of a local variation relative to a dimension of at least one contrasted element.

2. The method as claimed in claim 1, wherein the contrasted elements are alternate dark and light bands defining between them parallel interface lines, the interface lines being oriented so as to form an angle of between 20° and 70° with an anticipated direction of a defect of the glazing in a predetermined zone of the glazing, or an angle between 20° and 60°, or between 40° and 60°, or approximately 45°.

3. The method as claimed in claim 1, wherein at least one of the quantities is a statistical quantity.

4. The method as claimed in claim 3, wherein the statistical quantity is chosen from the following quantities, taken in isolation or in any possible combination: a mean; a weighted mean; a median; a standard deviation; a number of occurrences above or below a reference value; and a maximum or a minimum.

5. The method as claimed in claim 1, wherein the local variation of the at least one line representative of a principal orientation of the at least one contrasted element comprises a calculation of o(Pk+s)−o(Pk), where s is a chosen step, and where o(Pk) is a value for the orientation of the at least one line representative of a principal orientation of the at least one contrasted element at pixel Pk of index k.

6. The method as claimed in claim 5, wherein the at least one line representative of a principal orientation of the at least one contrasted element is one of the interface lines at least partially delimiting the at least one contrasted element.

7. The method as claimed in claim 5, wherein the at least one line representative of the principal orientation of a band is one of interface lines delimiting the band.

8. The method as claimed in claim 1, wherein the dimension is a local thickness of the at least one contrasted element or a distance between two contrasted elements.

9. The method as claimed in claim 8, wherein the local thickness is calculated by the distance between two adjacent interface lines.

10. The method as claimed in claim 8, wherein a degree of relative local variation of the dimension comprises calculating e(Pk+s)−e(Pk), where e(Pk) is a value of the dimension of the at least one contrasted element at pixel Pk of index k, and where s is a step of a degree of variation.

11. The method as claimed in claim 1, wherein the step of calculating is repeated for plural interface lines and/or plural contrasted elements.

12. The method as claimed in claim 1, wherein the step of calculating is repeated inside one or more predefined zones for analyzing the first image.

13. The method as claimed in claim 1, wherein the method is repeated with at least one supplementary image, different from the first image.

14. The method as claimed in claim 13, wherein the supplementary image is obtained for the test chart of which the contrasted elements are alternate dark and light bands defining between them parallel interface lines, but forming an angle of between 30° and 150° with a direction of the interface lines of the test chart used to obtain the first image, or an angle of between 60° and 120°, or between 80° and 100°, or approximately 90°.

15. The method as claimed in claim 14, wherein the interface lines of the test chart used for the supplementary image are oriented so as to form an angle of between 20° and 70° with an anticipated direction of a defect of the glazing in a predetermined zone of the glazing, or an angle between 20° and 60°, or between 40° and 60°, or approximately 45°.

16. The method as claimed in claim 1, wherein an angle of incidence between an apparatus that is capturing the first image and normal to the plane of the glazing lies between 0° and 90°, or between 40° and 70° for a lateral glazing unit of a motor vehicle.

17. The method as claimed in claim 1, wherein an angle of incidence between an axis of an apparatus that is capturing the first image and normal to the plane of the glazing is equal to an angle between the plane of the test chart and the plane of the glazing.

18. The method as claimed in claim 1, wherein the contrasted elements are one or more of bands, squares, and spots.

19. The method as claimed in claim 1, wherein the capturing the first image comprises:

exposing the glazing to the test chart; and digitally acquiring, via an apparatus with digital sensors, the first image reflected by the glazing toward the apparatus.

20. The method as claimed in claim 1, wherein the first image of the test chart produced in reflection by the glazing is obtained by a simulation from the outer surface of the glazing, or from a theoretical surface of the glazing, from a measured surface of the glazing, or from a surface obtained by simulation of the curvature of the glazing.

21. The method as claimed in claim 1, further comprising choosing whether to reject the glazing according to a result of the comparing step.

22. A method for producing a glazing unit comprising:

forming the glazing; and analyzing quality of the glazing formed, wherein the analyzing quality step implements the method as claimed in claim 1.

23. The method as claimed in claim 22, wherein the step of forming the glazing comprises shaping the glazing defining an anticipated direction of a defect of the glazing in a predetermined zone.

24. The method as claimed in claim 23, wherein the step of shaping the glazing comprises contacting with at least one roller, an anticipated direction of the defect being along an axis of the roller or perpendicular to this direction.

25. The method as claimed in claim 23, wherein the step of shaping the glazing comprises holding edges of the glazing, or pressing or allowing the glazing to sink under gravity, an anticipated direction of defects in a region of the edges being parallel to or perpendicular to the respective edge.

26. A device for analyzing quality of a glazing unit, comprising:

means for generating a digital first image of a test chart produced in reflection by an outer surface of the glazing in a direction away from the glazing; and a processing unit for processing the first image generated, the processing unit including a memory and a computer, wherein the memory includes computer executable instructions for executing the method as claimed in claim 1, the computer executable instructions calculating the quantities of the glazing from the first image generated, the quantities being representative of the deformation of the image of the test chart produced in reflection by the outer surface of the glazing.

27. The device as claimed in claim 26, wherein the means for generating the first image comprises a test chart and an apparatus with digital sensors, the test chart and the apparatus being arranged to respectively produce and acquire the first image of the test chart produced in reflection by the outer surface of the glazing, or the test chart being a screen and the device comprising a projector for projecting test chart patterns onto the screen.

* * * * *